United States Patent
Sedic (10) Patent No.: US 9,456,922 B2
(45) Date of Patent: Oct. 4, 2016

(54) PROPHYLACTIC HAVING A TEXTURED PATTERN

(71) Applicant: Filip Sedic, Shanghai (CN)

(72) Inventor: Filip Sedic, Shanghai (CN)

(73) Assignee: Lelo Inc., San Jose, CA (US)

( * ) Notice: Subject to any disclaimer, the term of this patent is extended or adjusted under 35 U.S.C. 154(b) by 358 days.

(21) Appl. No.: 13/666,925

(22) Filed: Nov. 1, 2012

(65) Prior Publication Data

US 2016/0038334 A1    Feb. 11, 2016

(51) Int. Cl.
*A61F 6/04*    (2006.01)
*B29C 39/26*    (2006.01)
*B29L 23/00*    (2006.01)

(52) U.S. Cl.
CPC .............. *A61F 6/04* (2013.01); *B29C 39/26* (2013.01); *A61F 2006/047* (2013.01); *A61F 2006/048* (2013.01); *B29L 2023/003* (2013.01)

(58) Field of Classification Search
CPC ...... A61F 6/04; A61F 6/08; A61F 2006/047; A61F 2006/048; A61F 2005/417; A61F 2006/044; A61F 5/41; A61L 31/048; A61L 31/14; A61L 2300/404; A61L 2300/606; A61L 2420/06; A61L 31/02
USPC .......................... 128/842, 844; 603/347–353; 604/347–353
See application file for complete search history.

(56) References Cited

U.S. PATENT DOCUMENTS

| | | |
|---|---|---|
| 2,285,981 A | 6/1942 | Johns |
| 2,288,840 A | 7/1942 | Raiche |
| 2,567,926 A | 9/1951 | Dunkelberger |
| 2,586,674 A | 2/1952 | Lonne |
| 2,670,736 A | 3/1954 | Dunkelberger |
| 2,696,209 A | 12/1954 | Varaney |
| 3,463,141 A | 8/1969 | Mozolf |
| 3,648,700 A | 3/1972 | Warner |
| 3,759,254 A | 9/1973 | Clark |
| 3,809,090 A | 5/1974 | Povlacs et al. |
| 4,074,712 A | 2/1978 | Wright |
| 4,553,968 A * | 11/1985 | Komis ................. 604/349 |

(Continued)

FOREIGN PATENT DOCUMENTS

| | | |
|---|---|---|
| CN | 1065391 A | 10/1992 |
| CN | 1071569 A | 5/1993 |

(Continued)

OTHER PUBLICATIONS

European Patent Office, Search Report and Opinion, European Patent Application No. 13190741.2, Dec. 3, 2013, six pages.

(Continued)

*Primary Examiner* — Michael Brown
(74) *Attorney, Agent, or Firm* — Fenwick & West LLP (57) ABSTRACT

A prophylactic device includes a base for receiving a portion of a body, a tip for containing body fluids, and a tubular body in between. The tubular body includes at least one area with a textured pattern, including lines running along the tubular body (e.g., lines running in at least three directions) that form shapes on the tubular body with portions of the lines forming edges of the shapes (e.g., circles, ellipses, polygons, etc.). The textured pattern forms a reinforcing mesh that wraps around the tubular body. A mold can be used for making the prophylactic device, where the mold includes different portions for receiving material(s), and is shaped to form the material(s) into the base, tip, and tubular body of the prophylactic device.

23 Claims, 5 Drawing Sheets

(56) References Cited

U.S. PATENT DOCUMENTS

| | | | |
|---|---|---|---|
| 4,798,600 A | | 1/1989 | Meadows |
| 4,829,991 A | | 5/1989 | Boeck |
| 4,856,534 A | | 8/1989 | Sorkin et al. |
| 4,881,553 A | * | 11/1989 | Grossman ............... 128/844 |
| 5,109,871 A | * | 5/1992 | Thornton ............... 128/844 |
| 5,513,652 A | * | 5/1996 | Schwartz ............... 128/842 |
| 5,513,654 A | | 5/1996 | Delson |
| 5,592,950 A | * | 1/1997 | Kopelowicz ............... 128/842 |
| 5,622,186 A | | 4/1997 | Schwartz |
| 5,779,621 A | | 7/1998 | Chaney |
| 5,816,249 A | * | 10/1998 | Kopelowicz ............. A61F 6/04 128/842 |
| 5,829,440 A | | 11/1998 | Broad, Jr. |
| 5,873,364 A | | 2/1999 | Kopelowicz |
| 6,182,661 B1 | | 2/2001 | Solanki et al. |
| D439,969 S | | 4/2001 | Strauss et al. |
| 6,308,708 B2 | | 10/2001 | Strauss et al. |
| 6,321,751 B1 | * | 11/2001 | Strauss et al. ............... 128/844 |
| 6,672,309 B1 | | 1/2004 | Al-Salem |
| 6,983,751 B2 | | 1/2006 | Osterberg |
| 7,086,403 B2 | | 8/2006 | Harrison et al. |
| 7,434,581 B1 | | 10/2008 | Reddy |
| 2012/0073580 A1 | | 3/2012 | Chua et al. |

FOREIGN PATENT DOCUMENTS

| | | | |
|---|---|---|---|
| CN | 1174019 | A | 2/1998 |
| CN | 1686064 | A | 10/2005 |
| CN | 200973775 | Y | 11/2007 |
| CN | 201182671 | Y | 1/2009 |
| CN | 201350149 | Y | 11/2009 |
| CN | 102228402 | A | 11/2011 |
| CN | 102247237 | A | 11/2011 |
| CN | 202173498 | U | 3/2012 |
| CN | 20218484 | * | 4/2012 |
| CN | 202184840 | U | 4/2012 |
| DE | 20 2004 018 991 | U1 | 3/2005 |

OTHER PUBLICATIONS

State Intellectual Property Office of the People's Republic of China, First Office Action, Chinese Patent Application No. 201310535629.1, Apr. 3, 2015, eighteen pages.

European Patent Office, Examination Report, European Patent Application No. 13190741.2, Aug. 3, 2015, four pages.

State Intellectual Property Office of the People's Republic of China, Second Office Action, Chinese Patent Application No. 201310535629.1, Sep. 15, 2015, nineteen pages.

State Intellectual Property Office of the People's Republic of China, Third Office Action, Chinese Patent Application No. 2013105356291, Apr. 12, 2016, eighteen pages.

State Intellectual Property Office of the People's Republic of China, Rejection Decision, Chinese Patent Application No. 201310535629.1, Jul. 18, 2016, seventeen pages.

* cited by examiner

PROPHYLACTIC HAVING A TEXTURED PATTERN

BACKGROUND

The present invention relates generally to prophylactic devices, and more particularly to a prophylactic device having a textured pattern.

A variety of different contraceptive devices are on the market today, but prophylactic devices, such as condoms, remain one of the most widely used and most popular contraceptives because of their convenience in use and ability to provide generally effective contraception and protection from sexually-transmitted diseases. Condoms can, however, have certain drawbacks and condom technology has made limited advances over the years. Some of the major contributors to the failure of condoms to provide contraception and disease protection include damage to or breakage of the condom and potential condom slippage during use. With a typical condom, if even a small tear is accidentally made (e.g., during usage of the condom or by a fingernail during application of the condom), the condom often will rip completely. The standard uniform latex design of the condom has no mechanism to prevent tears from propagating once started. Complete ripping of the condom during usage results in substantial and irreversible negative effects, with the condom losing most or all of its contraceptive or disease-protection ability. Other problems faced with condoms include the condom slipping off, since the typical smooth condom design can make it difficult to keep the condom securely in place. Condoms also sometimes fail to fit correctly and have an inability to provide a comfortable and secure fit regardless of the size of the wearer. Thus, there are multiple problems with current condom designs that still need to be solved.

SUMMARY

Embodiments include a prophylactic device having a textured pattern on the device that provides a variety of advantages. The textured pattern can increase the strength of the device and reduce the breakage rates, it can increase or decrease the elasticity of the device for different materials and different sections of the device, it can reduce slippage and provide better friction to help the device stay in place, and it can provide a tighter fit, regardless of the size of the wearer of the device. In addition, the textured pattern can make the device more pleasurable for its users. For example, the textured pattern around the pleasure glands can increase or decrease pleasure sensations, it can be present inside and/or outside the device to increase the comfort and sensitivity for the person wearing the device and for another person in contact with the outside of the device, and it can provide additional lasting lubrication, tingling sensations, spermicidal applications, and can sensitize or desensitize in a soluble way from the pattern itself. The textured pattern can also be in a gel or soluble form to protect against sexually-transmitted infections (STIs) or sexually-transmitted diseases (STDs), such as those caused by bacteria, viruses, fungi, parasites, and protozoans. Furthermore, the textured pattern can be used with or can itself include strength fibers or mesh members for increased strength of the prophylactic device. These are just a few examples of the advantages provided by the prophylactic device.

In one embodiment, the prophylactic device includes a closed distal tip for containing body fluids, a tubular body continuous with the distal tip, and an open proximal base continuous with the tubular body for receiving a portion of a body within. The tubular body includes at least one area comprising a textured pattern along the tubular body. The textured pattern comprises lines (e.g., markings, raised ridges, indentations, or other structures that provide a pattern in or on the device) running in at least three directions (e.g., vertically, horizontally, diagonally from left to right or from right to left, etc.) along the tubular body. The lines form shapes of the textured pattern (e.g., squares, triangles, circles, ellipses, rectangles, pentagons, hexagons, other polygons, etc.), and portions of the lines form the edges of the shapes. The textured pattern comprises a reinforcing mesh wrapping around the tubular body. This mesh enables containment of any breakage of the prophylactic device during use (e.g., while using the condom, while applying the condom, while removing the condom, etc.).

In an additional embodiment, there is a prophylactic device comprising a closed distal tip for containing body fluids therein, a tubular body continuous with the distal tip having at least one area comprising a textured pattern, and an open proximal base continuous with the tubular body for receiving a portion of a body within. The textured pattern is formed of a lattice of shapes having at least five sides, wherein the shapes are adapted to contain a tear of the prophylactic device within the sides of a single shape or within the sides of one or more other shapes adjoining the single shape.

The features and advantages described in this summary and the following detailed description are not all-inclusive. Many additional features and advantages will be apparent to one of ordinary skill in the art in view of the drawings, specification, and claims hereof.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

Figure 1:
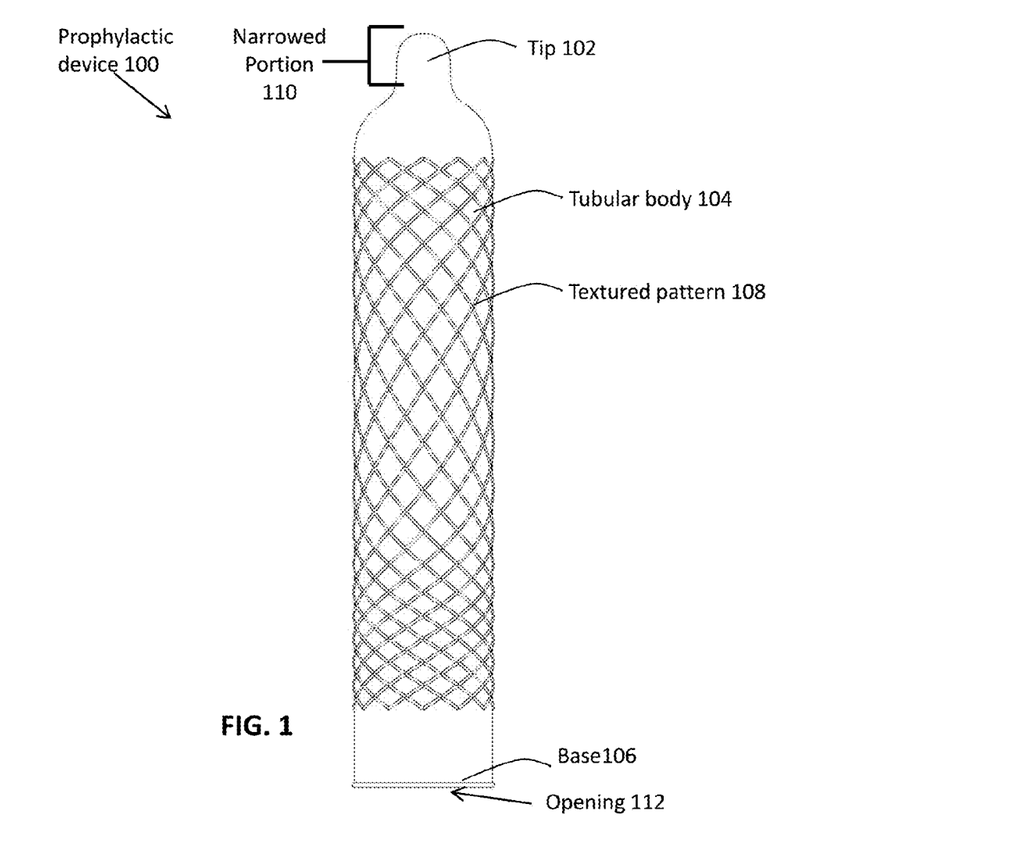
FIG. 1 is a side view of a prophylactic device, in accordance with embodiments of the invention.

Referring first to FIG. 1, there is shown a diagram illustrating the components of a prophylactic device 100, in accordance with an embodiment of the invention. In the embodiment of FIG. 1, the prophylactic device 100 includes a tip 102, a tubular body 104, and a base 106. The tubular body 104 includes a textured pattern 108. In some embodiments, the prophylactic device is a condom.

The tip 102 can be a closed distal tip for containing body fluids therein. The tip 102 has a narrowed portion 110 for containing body fluids. When the device 100 is applied to a portion of the body, such as the male penis, the tip of the body is inserted into the base 106, through the tubular body 104, and to the distal tip 102. Thus, the narrowed portion 110 sits against the body open for catching and containing body fluids inside.

The base 106 can be an open proximal base continuous with the tubular body for receiving a portion of the body (e.g., the male penis) within. The body can be inserted into the opening 112 of the base.

The tubular body 104 is continuous with the distal tip 102 and has at least one area comprising a textured pattern 108 along the tubular body 104. The portion of the body is contained within this tubular structure, and the textured pattern 108 thus wraps around this portion of the body.

The textured pattern 108 can cover any portion of the prophylactic device 100. In the embodiment of FIG. 1, textured pattern is shown covering a middle portion of the device 100. However, it can also cover a bottom or top portion of the device 100. In some embodiments, the textured pattern 108 can extend all the way to the tip 102 of the device 100 and/or all the way to the base 106 of the device 100, or it can be positioned as shown in FIG. 1 with a space in between the pattern 108 and the base 106/tip 102. In some embodiments, the textured pattern 108 covers 50% or 75% of the device 100 or more than 50% or 75%, though other percentages of coverage are also possible (e.g., less than 1%, 2%, 10%, 20%, 30%, 45% 60%, 78%, 90%, 100%, or any values or fractional values in between these numbers, or any ranges including one or two of these numbers bounding the ranges). For example, the textured pattern 108 can wrap around and cover a middle one-half portion of the device 100. The textured pattern 108 also may not be continuous, but can appear in disconnected portions along the device 100, such as in strips along the device. The pattern 108 can further be focused on one side, such as a front or back of the device 100. The pattern 108 can also appear in spots or pieces anywhere along the device 100, such as circular or square patches that may be connected or not. These are just a few examples of how the textured pattern 108 can be arranged on the device 100, though other designs are also possible.

The textured pattern 108 can be created in the prophylactic device 100 in a number of manners. In one embodiment, the textured pattern 108 is a pattern that is molded into the tubular body. For example, the pattern can be ridges or indentations formed on an inner or outer surface of the device 100. This can be performed using a device mold, such as that described later in this application. In another embodiment, the textured pattern 108 is embedded within the device 100. For example, the pattern can be made up of fibers or a mesh that is embedded within layers of the device 100, or is placed on an outer or inner surface of the device 100. The pattern can also be made with a separate mold and embedded or otherwise attached to the device 100.

The prophylactic device can be made of various materials. In one embodiment, the entire device 100 is composed of latex, polyurethane, polyisoprene, natural skin or animal tissue (e.g., intestines), rubber, or other materials. The device 100 can also be composed of more than one material. For example, the device 100 may be composed of latex, but the textured pattern might be made up of a mesh or fibers of a different material. The textured pattern itself might include more than one material, including a material on the surface of the pattern and a different material embedded within the pattern. Different types of the device 100 can have different materials to provide varying elasticity to allow for sizing of the device 100. Similarly, different portions of the same device can include different materials to provide varying elasticity within the device at different areas.

The textured pattern 108 can provide a number of advantages and can have a number of designs. For example, the textured pattern 108 can comprise fibers or a mesh within the tubular body 106, enabling increased tensile strength to the prophylactic device 100 in comparison to a prophylactic device without the textured pattern. This thus makes the device 100 stronger than other prophylactic devices and less likely to break or tear. As another example, the textured pattern 108 can provide different elasticity to the device 100. The portion of the prophylactic device 100 with the textured pattern 108 can have a different elasticity than the portion of the device 100 without the textured pattern 108. The textured pattern 108 can also enable a tighter fit around the body in comparison to a device without the textured pattern. The textured pattern 108 can also enable a tighter fit around the body in comparison to a device without the textured pattern, or the pattern can be used to provide greater elasticity so that a one-size-fits-all design can be made. The textured pattern 108 can further be arranged to provide friction against the portion of the body inside the device 100 (e.g., a male penis) or a portion of a body outside of and in contact with the device (e.g., part of the female anatomy) to reduce slipping of the device 100 in comparison to a prophylactic device without the textured pattern. In addition, the textured pattern 108 can assist in preventing fluids from exiting the condom by providing structures or walls within the condom that prevent fluid from coming up from the tip. The textured pattern 108 can also help trap fluids in the textured areas (e.g., within the boundaries of the shapes formed in the pattern). Similarly, the textured pattern 108 can assist in keeping the condom lubricated by trapping lubricant in the textured areas or pockets in the textured pattern, which lowers the risk of damaging the condom while being carried in a pocket or wallet and provides a good feel to the condom. The textured pattern 108 can also be arranged on both an inside and an outside of the prophylactic device 100 to provide additional stimulation to the body within the device 100 touching the inner surface and to a body outside of and in contact with an outer surface of the device 100.

Figure 2:
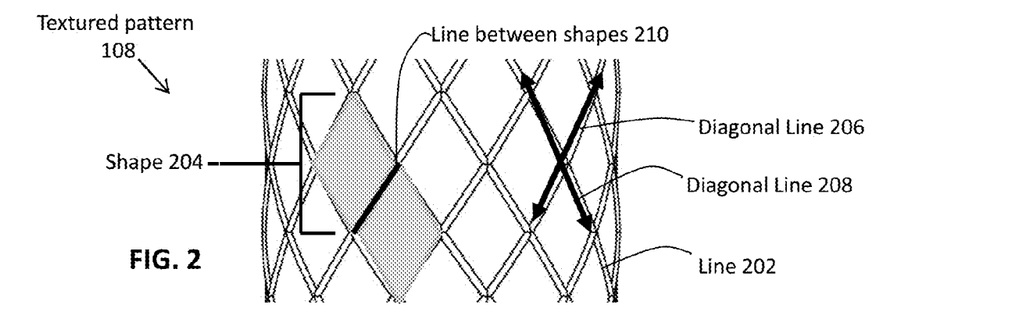
FIG. 2 is an enlarged side view of a textured pattern of a prophylactic device, in accordance with embodiments of the invention.
Figure 3:
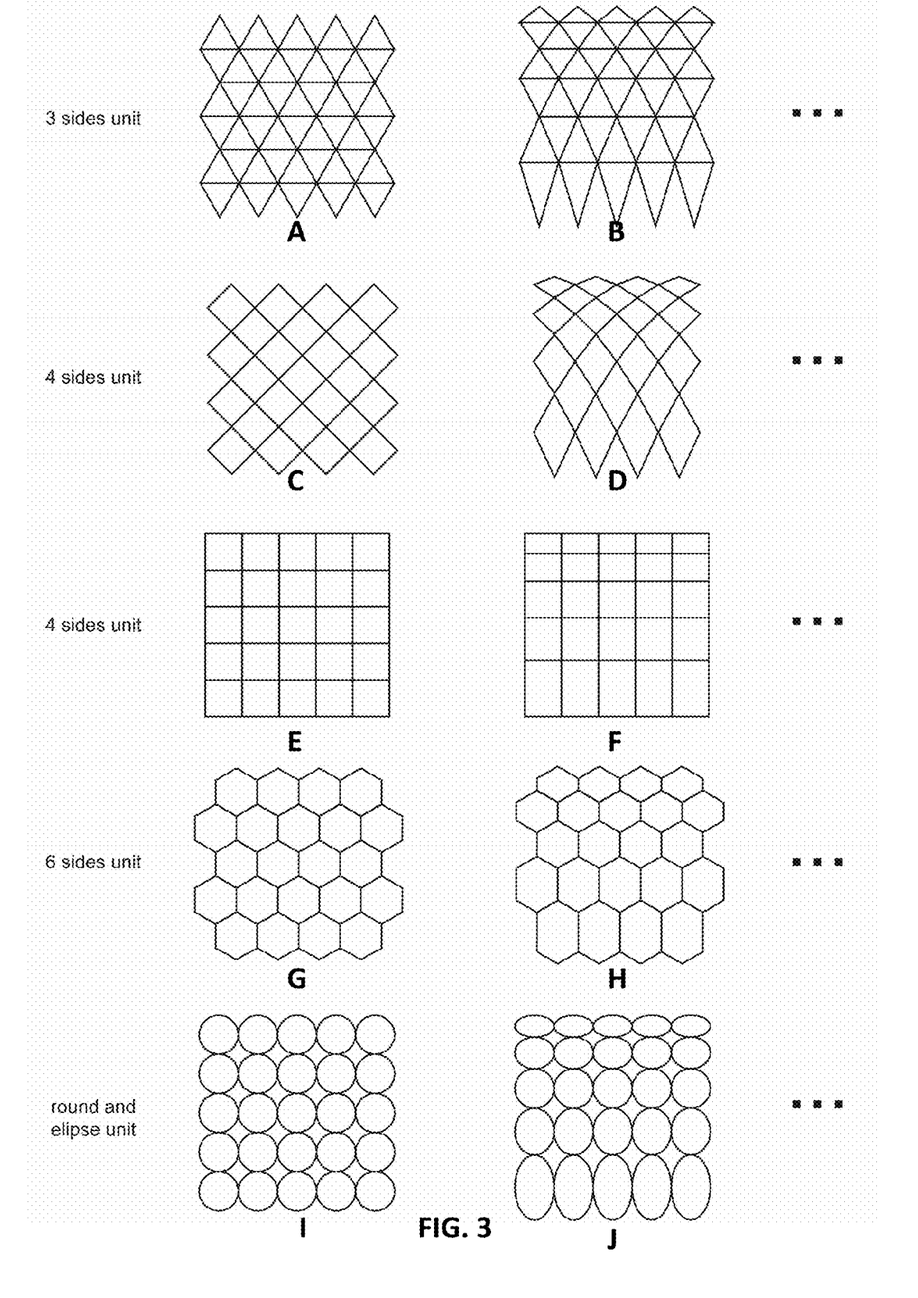
FIGS. 3A-J are enlarged side views of textured patterns of a prophylactic device, in accordance with embodiments of the invention.

FIG. 2 is an enlarged side view of a textured pattern of a prophylactic device, in accordance with an embodiment of the invention. The textured pattern 108 includes lines 202 running along the tubular body 104. The lines form shapes 204 in the textured pattern 108. The shapes shown in FIG. 2 are diamond shapes, though other shapes are also possible, as are illustrated in FIG. 3. One or more of the lines can include solid lines, broken lines, dots or other structures formed as a line, or other designs for providing a structure that can form the edge of a shape. One or more of the lines can be straight or curved along all or any portion, they can be grouped together or separate, they can intersect or not, they can have different thicknesses or widths (e.g., thick enough to form a band or thin enough to be hair-like), different lengths, different heights (e.g., for ridges or indentation lines), and the width, length, and height can vary across a single device, among other design variations.

Portions of the lines 202 form edges of the shapes. In fact, two shapes can share a single line 202, as is shown in FIG. 2 with line 210 being shared between two diamond shapes 204. The lines 202 can run in various directions or along various axes on the device. For example, FIG. 2 shows diagonal lines 206 and 208 illustrating two directions in which the lines can run. Similarly, the lines can run vertically or horizontally. A line 202 can wrap all the way around the device 100 or only partially around the device. The lines 202 can run along an X, Y, or Z axis. FIG. 2 shows continuous diagonal lines 206, 208 that wrap all the way around the device 100 to form a part of multiple diamond shapes 204. However, the lines 202 can be shorter and form only a portion of one or two shapes, or of just a few shapes. In some embodiments, the lines 202 are formed as fibers or a reinforcing mesh wrapping around the tubular body 104 enabling containment of breakage of the prophylactic device during use, as is shown in later figures.

FIGS. 3A-J are enlarged side views of textured patterns of a prophylactic device, in accordance with embodiments of the invention. Any of these patterns can be included on a prophylactic device, such as device 100 as textured pattern 108. For example, the pattern 108 shown in FIG. 1 could be replaced entirely or in part with the pattern of FIG. 3G. These are just some examples of textured patterns, though other patterns can also be used, such as patterns that include pentagons, heptagons, octagons, and any other polygon. The shapes can be irregular or have unequal sides. A single pattern can include multiple shapes, such as hexagons and diamonds. The shapes can also be composed of shapes that include at least 3, 4, 5, 6, 7, 8, 9, 10 sides, among other examples. Any of the patterns can be turned in any direction such that the lines run at a different angle relative to the device than is shown. Any line angle relative to a vertical or horizontal axis of the device is possible (e.g., 5, 10, 20, 30, 40, 50, 60, 70, 80, 90, 100, 130, 150, 170 degree angles, or any values or fractional values in between or any ranges including any of these numbers).

FIGS. 3A and B show patterns that include a number of triangles formed from lines running in three directions, two diagonal directions and one horizontal direction. These patterns are similar to the textured pattern 108 of FIG. 1, but the diamond shapes are bisected by horizontal lines wrapping around the device. FIG. 3B illustrates that the triangle shapes can be irregular in size, in this case with larger, vertically stretched triangles at the bottom in comparison to the top of the figure. The shapes in these figures are three-sided shapes.

FIGS. 3C and D show patterns that are similar to the textured pattern 108 of FIG. 1, forming diamond shapes. FIG. 3D illustrates that these diamond shapes can be irregular or can be larger or more stretched in certain areas. Lines run diagonally in two directions opposite one another along the device to form the diamond shapes. The shapes in these figures are four-sided shapes.

FIGS. 3E and F show patterns that are similar to the pattern 108 of FIG. 1, but the lines run vertically and horizontally instead of diagonally, and so the shapes formed are square shapes. These can also be rectangular shapes. FIG. 3F illustrates irregularity in the shapes, including some rectangles and some squares. The shapes in these figures are four-sided shapes.

FIGS. 3G and H show patterns that are formed of hexagons. This pattern is a honeycomb lattice or chicken-wire design. The lines run in three directions including two diagonal directions and one vertical direction. FIG. 3H shows that the hexagons can be irregularly sized or stretched in certain areas. The shapes in these figures are six-sided shapes.

FIGS. 3I and J show patterns that are formed of circles and/or ellipsoids. These round or ellipsoid shapes are formed of curved lines. The lines run in multiple directions to form the curved design of each shape.

Figure 4:
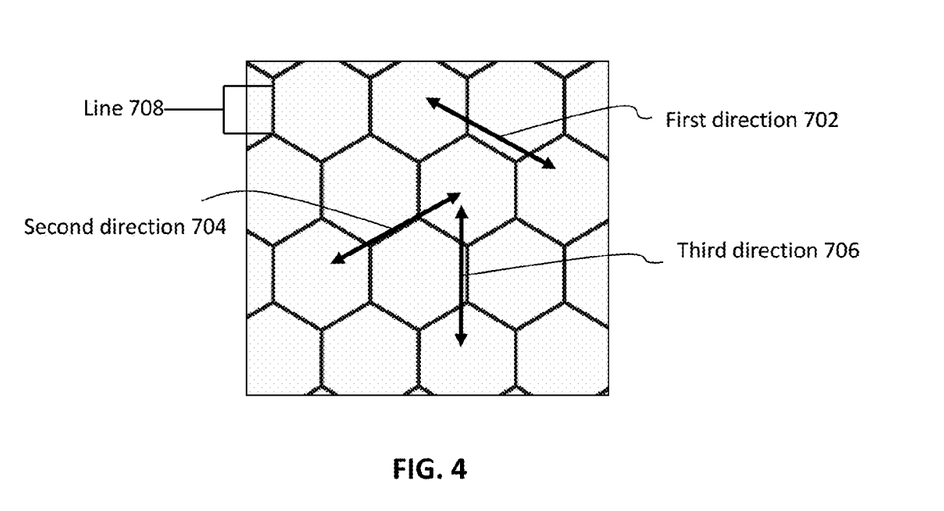
FIG. 4 is an enlarged side view of a textured pattern showing directional lines, in accordance with embodiments of the invention.

FIG. 4 is an enlarged side view of a textured pattern showing directional lines, in accordance with embodiments of the invention. Specifically, the pattern illustrated is the one shown in FIG. 3G with the honeycomb lattice. This figure shows that the lines run in a first, second, and third direction 702, 704, 706. Each line 708 forms a portion of at least two shapes in the pattern. Unlike the diamond pattern of FIG. 1 that shows a single line wrapping around the device to form a portion of multiple diamonds, the lines 708 in this pattern are shorter and form only one side of two of the hexagons. The hexagon pattern could also be turned such that none of the lines run vertically, and they all run at an angle relative to a vertical or horizontal axis of the device, where the vertical axis runs from the tip to the base of the device, and the horizontal axis runs from side to side of the device (or wraps around the tubular body of the device). The hexagons in FIG. 4 generally share six edges with other hexagons in the pattern. None of the edges are formed by a continuous line running in a single direction across more than one shape.

Figure 5:
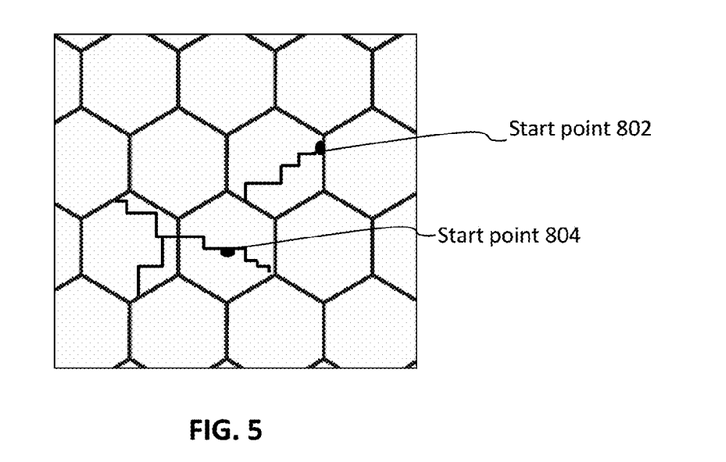
FIG. 5 is an enlarged side view of a textured pattern showing contained breakage, in accordance with embodiments of the invention.

FIG. 5 is an enlarged side view of a textured pattern showing contained breakage, in accordance with embodiments of the invention. The upper break shows a start point 802 of the break at an edge of one of the hexagons. The tear has spread across the hexagon, but stopped at another edge of the hexagon. Thus, the break is contained within a single shape in the pattern. The lower break shows a start point 804 in the middle of one of the hexagons, and this break has spread in more than one direction and has spread across to an adjoining hexagon. However, the break is still contained within these two hexagons and has not propagated further in the device. In some embodiments, the textured pattern or a mesh or fibers in the pattern ensure that tears such as these do not propagate very far in the device. In some embodiments, the shapes are arranged such that breakage of the device within one of the shapes is contained within the edges of the shape or one or more other shapes adjoining the shape. In other embodiments, the breakage is contained within a certain number of the shapes, such as three, four, five, six, seven, and other numbers of shapes. In this manner, the contained breakage can prevent the device 100 from completely ripping or falling apart, allowing the device to still contain most or all of the fluids within. Thus, the safety of the device is enhanced, even if it is torn.

Figure 6:
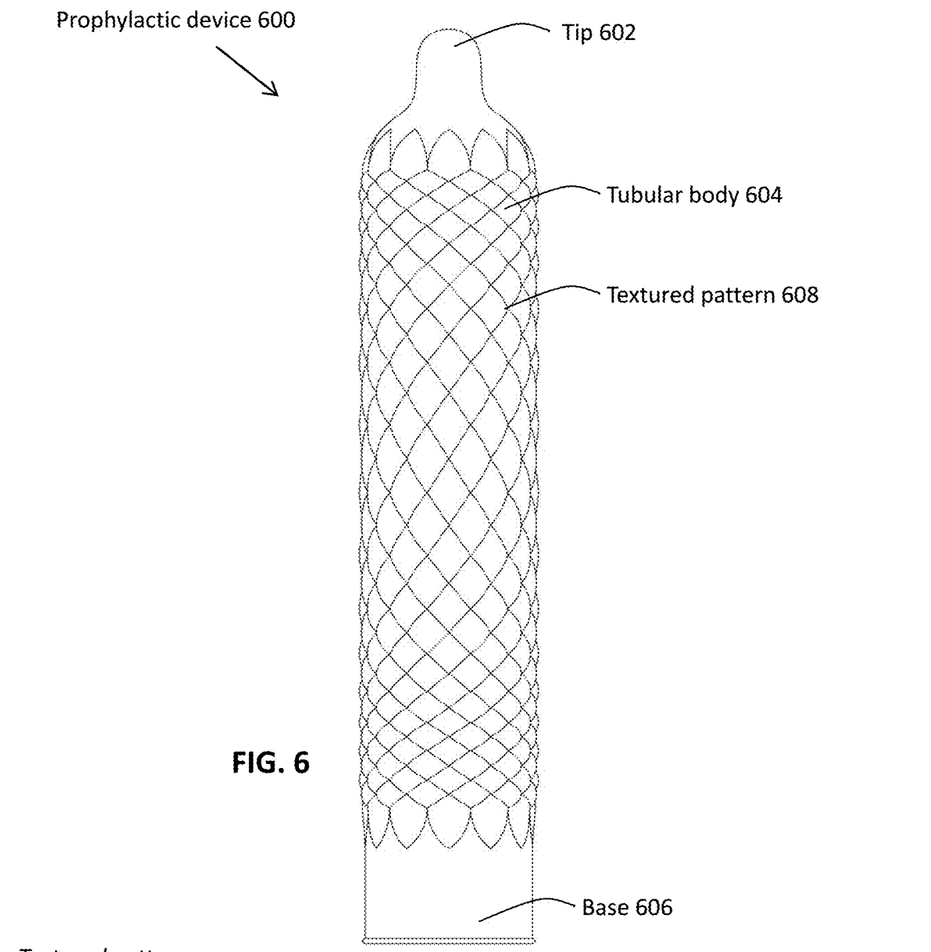
FIG. 6 is a side view of a prophylactic device with a pillow design, in accordance with embodiments of the invention.

FIG. 6 is a side view of a prophylactic device with a pillow design, in accordance with an embodiment of the invention. The prophylactic device 600 includes a tip 602, a tubular body 604, and a base 606. These structures can have generally the same features and characteristics as the tip 102, the tubular body 104, and the base 106 of FIG. 1, thus those features/characteristics are not re-described here. The device 600 also includes a textured pattern 608, which can have generally the same features and characteristics of textured pattern 108. In this case, however, the textured pattern 608 is raised in the center of each shape to form a pillow design.

Figure 7:
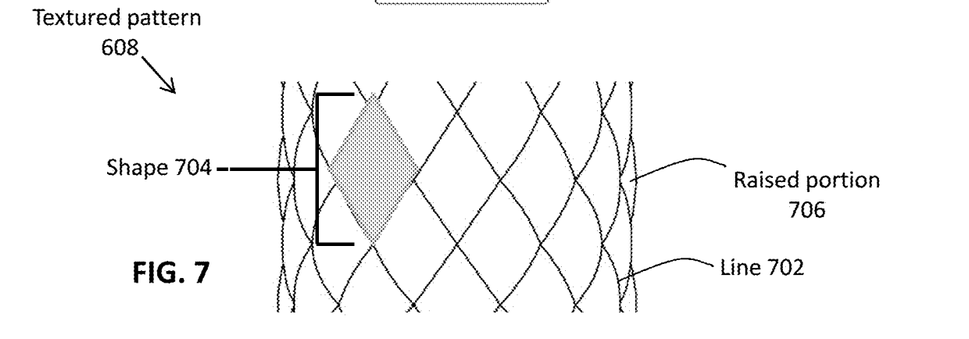
FIG. 7 is an enlarged side view of a textured pattern of a prophylactic device with a pillow design, in accordance with embodiments of the invention.

FIG. 7 is an enlarged side view of a textured pattern of a prophylactic device with a pillow design, in accordance with an embodiment of the invention. This figure illustrates the lines 702 that form the shapes in the device 600 and illustrates the shapes 704 themselves. The shapes can be any of the shapes shown in FIG. 3 and so the pattern 608 can be any of the FIG. 3 patterns. FIG. 7 also illustrates the raised portion 706 in the center of the diamond shapes of the pattern 608, which tapers inward toward the four edges of the diamond. The pillow design provides additional texture to the device, which can provide stimulation to a body in contact with the texture. The pillows can be formed with the raised portion 706 facing outward, as shown in FIG. 7, facing inward, or both. Thus, the pillows can stimulate a body inside or outside of the device 600.

Figure 8:
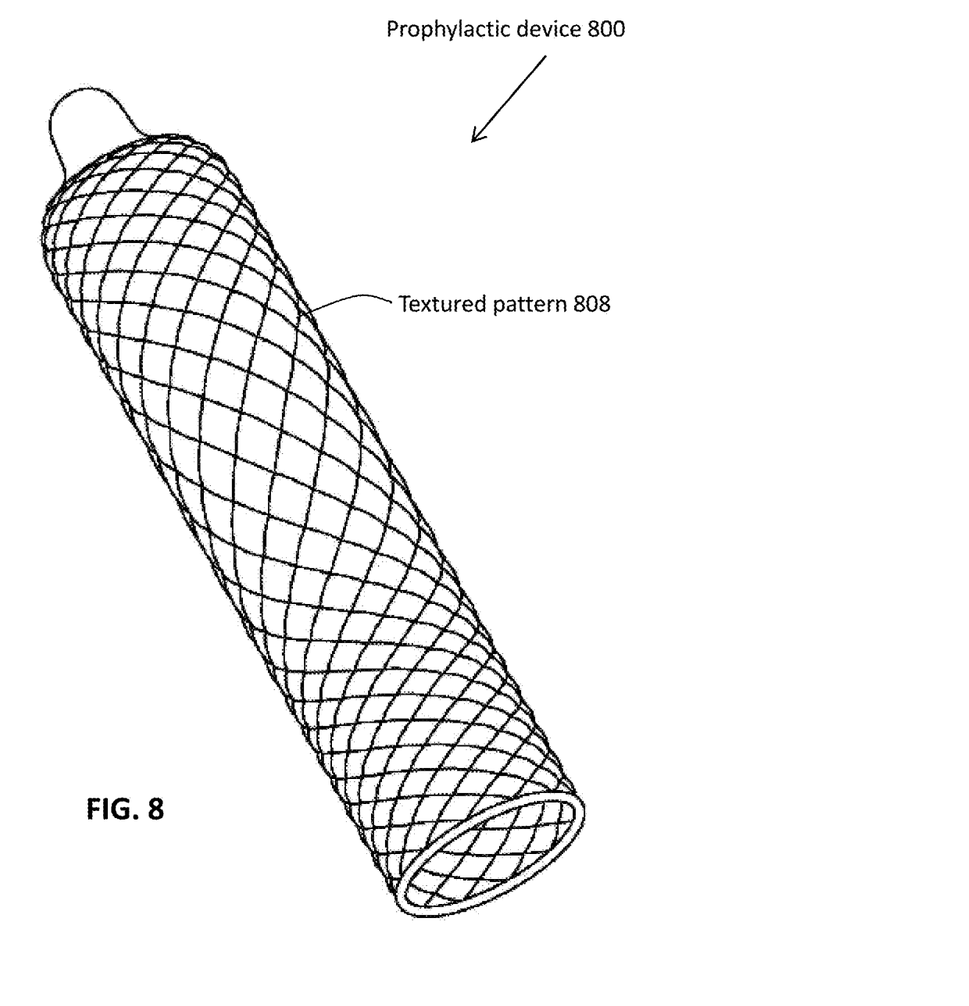
FIG. 8 is an isometric view of a prophylactic device with a pillow design, in accordance with embodiments of the invention.

FIG. 8 is an isometric view of a prophylactic device with a pillow design, in accordance with embodiments of the invention. In this prophylactic device 800, there is again a pillow type textured pattern 808, with the center of each shape raised. This figure also illustrates how the textured pattern 808 can wrap all the way from the tip of the device to the base, rather than being present only in a middle section of the device, as is shown in FIG. 6.

The prophylactic device can be made using a mold. In one embodiment, the mold includes a first area for receiving material and shaped to form the received material into at least a portion of a distal tip of a prophylactic device, a second area continuous with the first area for receiving material and shaped to form the received material into at least a portion of a tubular body continuous with the distal tip, and a third area continuous with the second area for receiving material and shaped to form the received material into at least a portion of a proximal base continuous with the tubular body. The mold can be a single structure into which material is poured to form an inner and outer surface of the device. The mold can also be a two-part structure (or a multi-part structure) with one side of the mold forming an outer surface of the device and the other part forming an inner surface. The prophylactic devices can also be made using a dipping process, and the texture of the condom achieved only by changing the mold.

The mold can be designed to form any of prophylactic devices 100, 600, and 800. The mold can be designed to be used in forming a device that has a textured pattern, such as those described above, including lines that run in at least two, three, four, five, etc. directions to form shapes with portions of the lines forming edges of the shapes. The textured pattern can form a reinforcing mesh on or in the tubular body for containment of breakage of the prophylactic device during use.

In some embodiments, the mold itself forms the textured pattern. The second area or another portion can include indentations or ridges capable of forming the received material into the textured pattern. In other embodiments, the textured pattern can be formed by adding a mesh or fibers to the device. Thus can be done in the mold or separate from the mold. The mesh/fibers can be positioned on an outer or inner surface of the device, or can be embedded within the device (e.g., between an outer and inner layer of the device). As one example, material can be placed into the mold to form an outer layer of the device, the mesh can be laid down on this material (possibly after it has solidified or dried somewhat or completely), and another layer of material can be placed on top of the mesh to form an inner layer of the device. Similarly, the mold could be dipped in material, a mesh added to the dipped material, and then a second dipping could occur to embed the mesh in the material. In further embodiments, a second mold or multiple other molds can be used to make the textured pattern, which can then be included in the device. In some embodiments, the condom can be made using standard condom making techniques, but the mold allows for the textured pattern to be provided on the condom.

While various embodiments have been described above, it should be understood that they have been presented by way of example only, and not limitation. For example, any of the components may employ any of the desired functionality set forth hereinabove. The functions can be distributed differently across the components or different functions can be combined into one component. The prophylactic devices and molds can be designed to have a variety of different shapes, sizes, designs, etc., and the embodiments shown herein are simply examples of some such shapes, sizes, and designs. Thus, the breadth and scope of a preferred embodiment should not be limited by any of the above-described exemplary embodiments.

What is claimed is:

1. A prophylactic device comprising:
a closed distal tip for containing body fluids therein;
a tubular body continuous with the distal tip having at least one area comprising a textured pattern along the tubular body, the textured pattern molded onto a surface of the tubular body and comprising lines running in at least three directions along the tubular body, the lines forming a plurality of shapes with portions of the lines forming edges of the shapes, wherein none of the edges of the shapes are formed by a continuous line running in a single direction across more than one shape, the textured pattern comprising a reinforcing mesh wrapping around the tubular body; and
an open proximal base continuous with the tubular body for receiving a portion of a body within.

2. The prophylactic device of claim 1, wherein the plurality of shapes are a plurality of hexagons.

3. The prophylactic device of claim 1, wherein the plurality of shapes are shapes that include at least five sides.

4. The prophylactic device of claim 1, wherein the plurality of shapes are shapes that include at least six sides.

5. The prophylactic device of claim 1, wherein the textured pattern is a honeycomb lattice.

6. The prophylactic device of claim 1, wherein at least some of the lines include portions that are arranged vertically from the distal tip to the proximal base.

7. The prophylactic device of claim 1, wherein the textured pattern wraps around and covers at least a middle one-half portion of the prophylactic device.

8. The prophylactic device of claim 1, wherein the lines form edges of the plurality of shapes and wherein most of the shapes share at least five edges with other of the shapes.

9. The prophylactic device of claim 1, wherein the textured pattern covers more than 50% of the prophylactic device.

10. The prophylactic device of claim 1, wherein the textured pattern covers more than 75% of the prophylactic device.

11. The prophylactic device of claim 1, wherein at least some of the plurality of shapes are of different sizes.

12. The prophylactic device of claim 11, wherein at least some of the plurality of shapes are irregular polygons that are stretched relative to a corresponding regular polygon in a direction parallel to an axis extending from a base to a tip of the prophylactic device.

13. The prophylactic device of claim 1, wherein each of the shapes has a plurality of edges and wherein the shapes are arranged such that breakage of the prophylactic device within one of the shapes is contained within the edges of the shape or one or more other shapes adjoining the shape.

14. The prophylactic device of claim 1, wherein the plurality of shapes are raised in a center of each shape forming a pillow pattern.

15. The prophylactic device of claim 1, wherein a portion of the prophylactic device with the textured pattern has a different elasticity than a portion of the prophylactic device without the textured pattern.

16. The prophylactic device of claim 1, wherein the textured pattern enables a tighter fit around the portion of the body in comparison to a prophylactic device without the textured pattern.

17. The prophylactic device of claim 1, wherein the textured pattern is arranged to provide friction against the portion of the body to reduce slipping of the prophylactic device in comparison to a prophylactic device without the textured pattern.

18. The prophylactic device of claim 1, wherein the textured pattern is molded on both an inside and an outside of the prophylactic device.

19. The prophylactic device of claim 1, wherein the lines running in at least three directions comprise at least two diagonal directions and at least one horizontal direction.

20. The prophylactic device of claim 1, wherein the lines running in at least three directions comprise at least two diagonal directions and at least one vertical direction.

21. A prophylactic device comprising:
a closed distal tip for containing body fluids therein;
a tubular body continuous with the distal tip having at least one area comprising a textured pattern formed of a lattice of shapes having at least five sides, wherein none of the sides of the shapes are formed by a continuous line running in a single direction across more than one shape, the textured pattern molded onto a surface of the tubular body; and
an open proximal base continuous with the tubular body for receiving a portion of a body within.

22. The prophylactic device of claim 21, wherein the shapes are adapted to contain a tear of the prophylactic device within the sides of a single shape or within the sides of one or more other shapes adjoining the single shape.

23. A prophylactic device comprising:
a closed distal tip for containing body fluids therein;
a tubular body continuous with the distal tip having at least one area comprising a textured pattern along the tubular body, the textured pattern molded onto the tubular body and comprising lines running in at least three directions along the tubular body, the lines forming a plurality of shapes with portions of the lines forming edges of the shapes, wherein none of the edges of the shapes are formed by a continuous line running in a single direction across more than one shape, wherein:
the textured pattern comprises a reinforcing mesh wrapping around the tubular body, and
the plurality of shapes are raised in a center of each shape forming a pillow pattern; and
an open proximal base continuous with the tubular body for receiving a portion of a body within.

* * * * *